United States Patent [19]
Johnson et al.

[11] Patent Number: 5,263,962
[45] Date of Patent: Nov. 23, 1993

[54] BALLOON CATHETER AND METHOD OF USING THE SAME

[75] Inventors: Thomas R. Johnson, Milford; Andrew L. Cote, Sr., Peterborough, both of N.H.

[73] Assignee: Johnson Medical Development Corp., Nashua, N.H.

[21] Appl. No.: 794,562

[22] Filed: Nov. 19, 1991

Related U.S. Application Data

[63] Continuation-in-part of Ser. No. 616,630, Nov. 21, 1990, abandoned.

[51] Int. Cl.$^5$ .......................................... A61M 29/02
[52] U.S. Cl. .................................... 606/192; 128/4; 128/7
[58] Field of Search ............... 606/192, 194; 604/96; 128/4, 7

[56] References Cited

FOREIGN PATENT DOCUMENTS

| | | |
|---|---|---|
| 0283661 | 1/1988 | European Pat. Off. . |
| 0345051 | 6/1989 | European Pat. Off. . |
| 0366478 | 10/1989 | European Pat. Off. . |
| 2380786 | 2/1978 | France . |

*Primary Examiner*—Michael H. Thaler
*Attorney, Agent, or Firm*—Hayes, Soloway, Hennessey & Hage

[57] ABSTRACT

A balloon catheter is provided for treatment of hypertrophy of the prostate. The balloon is formed in a noncompliant transparent plastic sleeve fitted over a transparent plastic lumen. The distal end of the sleeve is secured to a fitting slidably mounted on the lumen.

10 Claims, 3 Drawing Sheets

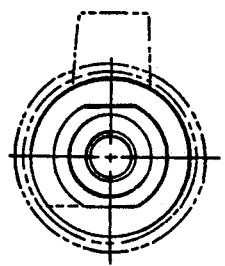
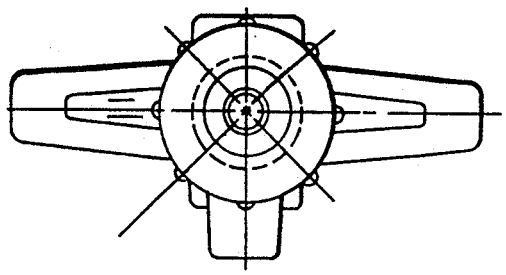
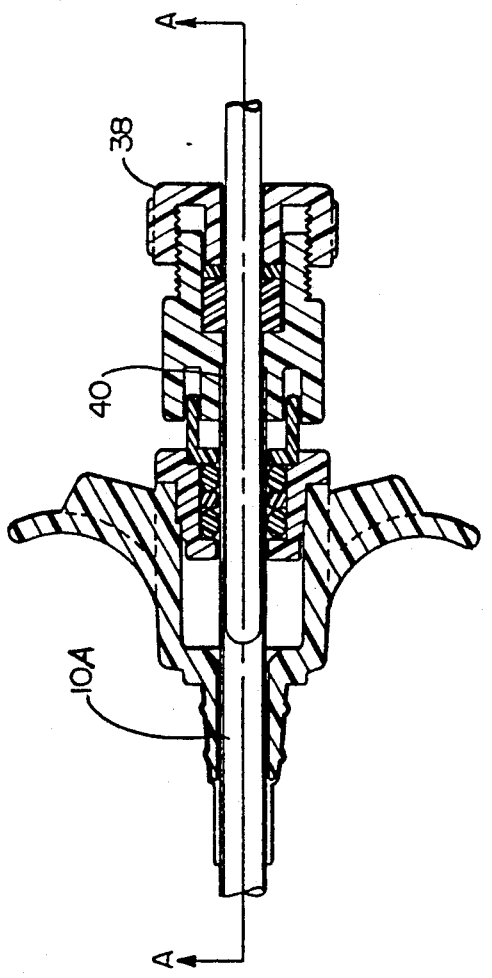
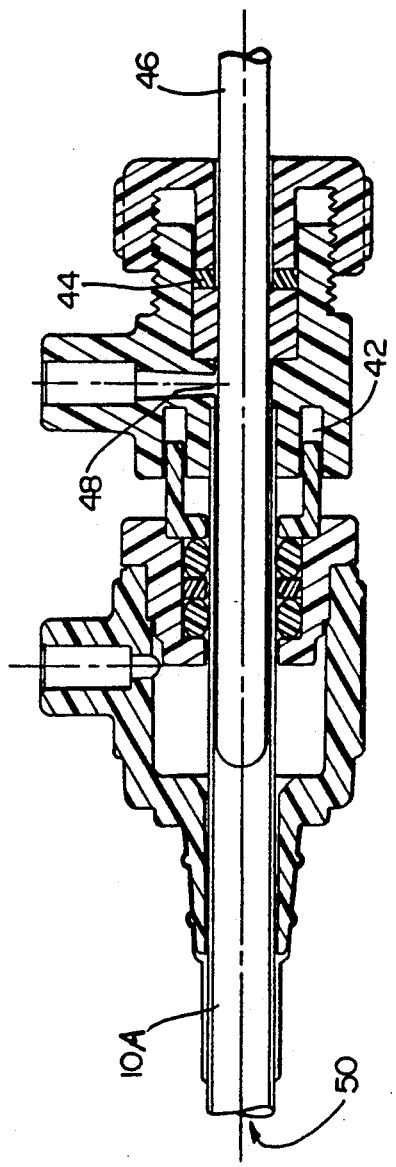

BALLOON CATHETER AND METHOD OF USING THE SAME

CROSS-REFERENCE TO RELATED APPLICATION

This application is a continuation-in-part of application Ser. No. 616,630 filed Nov. 21, 1990, now abandoned.

BACKGROUND OF THE INVENTION

The present invention is directed to a catheter for treatment of hypertrophy of the prostate, more specifically to the balloon dilatation of the prostate. Balloon dilatation has recently been introduced as an alternative procedure to transurethral resection of the prostate. This procedure involves inflating a balloon within the prostatic urethra to relieve outflow obstruction. Balloon dilatation generates a radial force against the prostate gland using a non-compliant balloon. The balloons used in this approach are essentially a modification of the non-compliant balloon developed for transluminal angioplasty of the coronary arteries.

One of the principal concerns in the use of balloon dilatation is the proper positioning of the balloon within the prostatic urethra. It must provide dilatation of the prostatic urethra, but it must not dilate the external sphincter. A number of techniques have been developed for providing this accurate positioning. One involves a radiopaque portion of the catheter carrying the balloon, another has a locator at the base of the dilatation balloon for digital palpation and a third has a marker on an external portion of the catheter which can be observed by a separate cystoscope which views the outside of the catheter through a separate catheter channel exterior to the main catheter.

The most pertinent patented prior art known to applicant is encompassed in the following patents:

| U.S. Pat. No. 4,490,421 | Levy | December 25, 1984 |
| U.S. Pat. No. 4,540,404 | Wolvek | September 10, 1985 |
| U.S. Pat. No. 4,660,560 | Klein | April 28, 1987 |
| U.S. Pat. No. 4,738,659 | Sleiman | April 19, 1988 |
| U.S. Pat. No. 4,779,611 | Grooters et al. | October 24, 1988 |
| U.S. Pat. No. 4,808,164 | Hess | February 28, 1989 |
| U.S. Pat. No. 4,893,623 | Rosenbluth | January 16, 1990 |
| U.S. Pat. No. 4,955,895 | Sugiyama et al. | September 11, 1990 |
| U.S. Pat. No. 5,007,898 | Rosenbluth et al | April 16, 1991 |
| German Patent No. 2653424 | Von Zeppelin D | June, 1978 |

BRIEF SUMMARY OF THE PRESENT INVENTION

The present invention provides an inexpensive catheter for precisely positioning and pressurizing a dilatation balloon within the prostatic urethra. It comprises an internal catheter tube formed of a transparent plastic having an open end. A non-compliant flexible sleeve is passed over the catheter tube, the sleeve being slightly larger, throughout most of its length, than the catheter tube and having a balloon section near the inner end of the tube which can be expanded, in a non-compliant fashion, to a predetermined diameter. The location of this balloon section is predetermined by the shape of the non-compliant plastic sleeve. At the outer end of the plastic sleeve is secured a first fluid tight fitting which surrounds and is slidably fitted to the outer end of said tube. An opening in the fitting permits pressurization fluid to be introduced into the fitting and the fitting provides a passage to the interior of the non-compliant plastic sleeve.

A second fluid tight fitting (flushing port) is positioned and bonded to the outer end of the transparent plastic tube. This flushing port also contains a fluid tight seal with respect to a viewing telescope or cystoscope lens which can be inserted into the interior of the transparent plastic tube. Accordingly, sterile fluid can be introduced into the interior of the transparent plastic tube, and at the same time said fluid surrounds the viewing telescope. In this manner the light traversing either from inside the tube to outside the catheter, or vice versa, is minimally refracted which provides improved transverse viewing by the telescope within the catheter tube for precise positioning of the catheter and its associated balloon. Furthermore, the sterile fluid serves to irrigate the particular body cavity in which the catheter is introduced.

One preferred form of the invention is provided by making the inner diameter of the inner end of the first fitting, surrounding the catheter tube, slightly larger than the diameter of the tube. The outer end of the first fitting is sealed to the tube by a fluid tight seal which also permits movement of the fitting along the tube parallel to and rotationally about its axis. Means are provided for permitting retraction of the fitting, to tension or wrap the dilatation balloon tightly onto the catheter tube, for ease of insertion and removal of the device from the urethra.

In the use of the device, a viewing telescope, which can view transversely from within the catheter tube, is inserted in the interior of the tube so as to observe the precise location of the catheter tube and its associated balloon with respect to the sphincter of the prostatic urethra. Sterile solution is then introduced from the second fluid tight fitting at the outer end of the plastic tube, which travels down the length of the interior of the plastic tube, surrounding the telescope, exiting at the open inner end of said tube. Accordingly, when the desired position is precisely obtained, as indicated by a mark on the plastic sleeve or tube, fluid pressure is introduced to the interior of the first fitting. The fluid passes between the front of this fitting and the tube and enters the interior of the plastic sleeve, thereby pressurizing the balloon to a predetermined pressure. Since the balloon is non-compliant it will create dilatation of the prostate to a predetermined amount. After the dilatation treatment is complete, the pressure is released and the catheter is removed. Prior to removal, the first fitting, which is secured to the outer end of the sleeve, is pulled backwards and twisted so as to collapse the balloon sleeve tightly against the tube, permitting ease of withdrawal.

In order to more fully understand the following detailed description of the invention, reference should be had to the accompanying drawings wherein:

FIGS. 3A, 3B and 3C are a diagrammatic schematic view of the assembled balloon catheter which contains a flushing port; and FIG. 4 is an enlarged diagrammatic schematic view of the first and second fluid tight fittings which respectively serve to pressurize the balloon to a predetermined pressure and provide sterile fluid to the interior of the tube.

Figure 1:
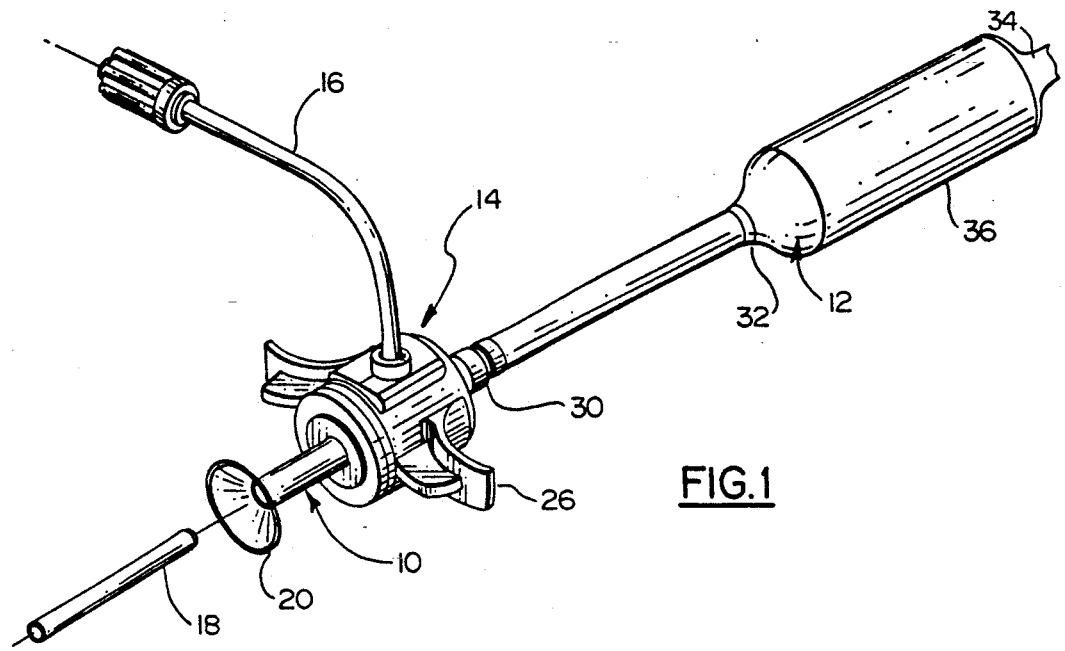
FIG. 1 is a diagramatic schematic view of the assembled balloon catheter in the absence of a flushing port.
Figure 2:
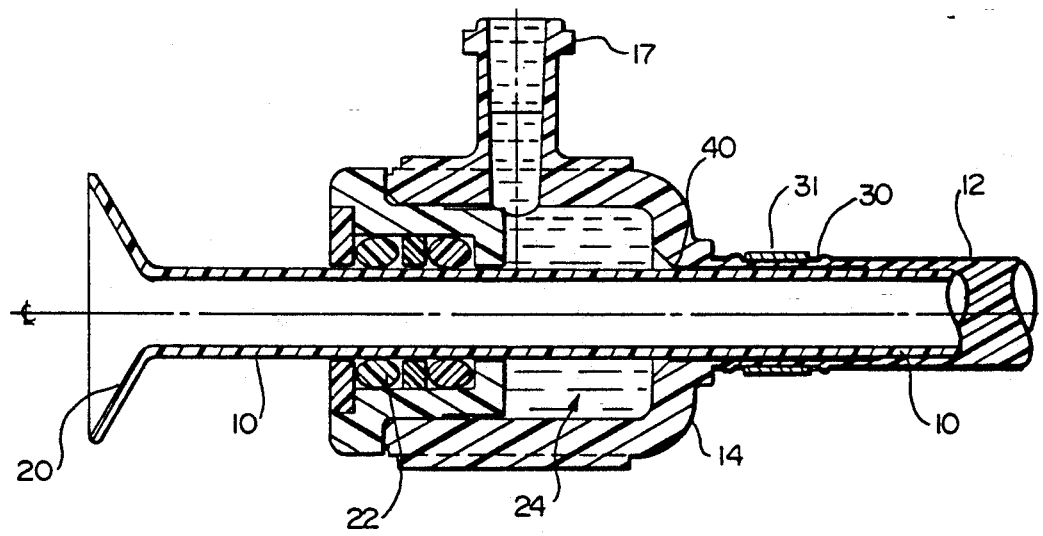
FIG. 2 is a diagramatic schematic sectional view of the outer end of the catheter showing the first fitting and seal between the outer end of the balloon and the slidable housing which permits pressurization of the balloon.

Referring now to FIGS. 1 and 2, the transparent catheter tube is illustrated at (10) supporting a transparent non-compliant balloon catheter sleeve (12). A fitting (14) forms a fluid tight seal (30) with the outer end of the balloon catheter sleeve (12). At the outer end of the fitting (14) there is a fluid tight seal (22) with the exterior surface of the tube (10). Pipe (16), terminating at an opening (17), (FIG. 2), provides means for introducing pressurizing fluid into a fluid chamber (24) inside the fitting. The flared opening (20) at the outer end of the catheter tube provides a means for inserting a telescope (18) which can provide radial viewing of and through the tube to permit proper positioning of a mark (32), on the plastic sleeve or tube of the balloon catheter, with respect to the prostatic sphincter. Handles (26) on the side of the fitting permit application of a withdrawal force to the fitting for the purpose of tensioning and wrapping the balloon catheter to make it closely hug the tube (10) for ease of insertion and withdrawal. It also permits positive placement of the balloon with respect to the prostatic sphincter.

As can be seen best from FIG. 1, the inner end of the balloon catheter sleeve has a small diameter (34) which is sealed or bonded liquid tight to the open inner end of the tube (10) and positions the balloon. At the other end of the balloon (36) are one or more marks (32), on the plastic sleeve or tube, which can be precisely positioned, by means of a viewing telescope, with respect to the prostatic sphincter. When the catheter is thus positioned, it can be inflated by applying fluid pressure through the tube (16) to the interior (24) of the fitting. While this pressurization takes place, the telescope can insure that the balloon does not move axially with respect to the prostatic sphincter.

Figure 5:
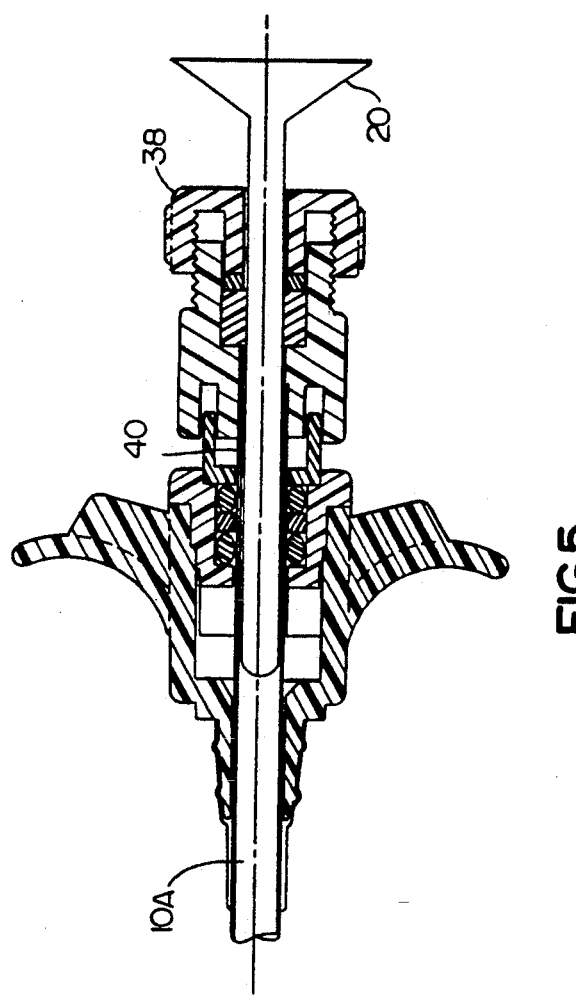
FIG. 5 is similar to FIG. 3 with the inclusion of an enlarged end.

As can be seen from FIG. 3, a second fluid tight fitting (38) is positioned at the outer end of the transparent plastic tube (10A) where said plastic tube is bonded and connected at 40 to said fitting. Referring now to FIG. 4, a sliding gap is provided for in the second fitting at (42) of about 0.3 inch. The second fluid tight fitting, or flushing port, forms a fluid tight seal (44) with the exterior surface of a viewing telescope (46) when said telescope has been inserted into the transparent plastic tube (10A). Accordingly, sterile fluid is delivered at opening (48) and travels down the exterior surface of the viewing telescope and into the tube (10A) and exits the device at (50). Accordingly, the presence of liquid as between the viewing telescope and the inner wall of the plastic tube prevents light from reflecting back from said wall or significantly refracting in traversing from inside the tube to outside the catheter, and vice versa, when positioning the device. In this manner localized distortions of the viewing telescope, when operating across an air interface, can be minimized. Alternatively, as shown in FIG. 5, tube 10A may also include an enlarged end 20.

In a preferred embodiment of the invention, the catheter tube is formed of transparent polyethylene terephthalate and the balloon is made of a transparent biaxially oriented polyethylene terephthalate film. A preferred method of making this type of non-compliant balloon is illustrated in U.S. Pat. No. 4,490,421 to Levy (assigned to Dupont). The fitting (14) can be made of any strong plastic such as a polycarbonate (e.g. "Lexan").

In one preferred embodiment of the invention the wall thickness of the balloon is 0.001-0.002 inch and the inflated diameter of the balloon is 0.98-1.18 inch. The tube diameter is preferably on the order of 0.20-0.23 inch and the wall thickness is preferably about 0.02-0.03 inch. The passage (40), (see FIG. 2), which permits pressurization of the interior of the balloon, is preferably formed by a difference in radius between the exterior of the tube and the interior of the forward end of the fitting of approximately 0.005-0.010 inch. The seal (30) is preferably provided by cementing the interior of the sleeve to the exterior of the forward end of the slidable fitting (14). If desired, an exterior sleeve, such as shown at (31), can be applied to assure a liquid tight joint between the fitting and the sleeve.

As can be seen from the above description, the present invention provides an inexpensive, disposable balloon catheter which can be precisely positioned and precisely inflated to a predetermined diameter. The balloon can be collapsed and pulled tightly around the tube for ease of insertion and withdrawal.

While one preferred embodiment of the invention has been described above, numerous modifications may be made without departing from the spirit of the invention.

We claim:

1. A prostate balloon dilation catheter comprising:
   a transparent plastic tube having an open inner end and an open outer end and including a viewing telescope insertable therein; and
   a non-compliant transparent flexible plastic sleeve of predetermined shape slidably fitted over the tube, a portion of said sleeve forming a dilation balloon having a diameter greater than said tube, the inner end of the sleeve closest to the inner end of the tube being provided with a liquid tight seal with the tube; and
   a first fitting surrounding and slidably fitted to the outer end of the tube, the outer end of the fitting closest to the outer end of the tube being provided with a liquid tight seal with the tube; and
   a liquid tight seal between the outer end of said transparent flexible plastic sleeve and the fitting; and
   means permitting introduction of dilation fluid to the interior of the fitting; and
   a liquid passage between the interior of the fitting and the interior of the sleeve to permit pressurization by the fluid of the dilation balloon; and
   a second fitting bonded to the outer end of the transparent plastic tube being provided with a second liquid tight seal with respect to the exterior surface of said viewing telescope inserted into said plastic tube; and
   means permitting introduction of sterile fluid to the interior of the second fitting; and
   a liquid passage between the interior of the second fitting and the exterior surface of said viewing telescope to permit the flow of fluid within the area between the transparent plastic tube and said telescope, said telescope providing radial viewing through the transparent plastic tube and sleeve.

2. The catheter of claim 1 wherein the open outer end of the transparent tube is enlarged to facilitate insertion of said viewing telescope for observation of the balloon with respect to the prostrate to be dilated.

3. The catheter of claim 1 wherein a handle is provided on the first fitting surrounding and slidably fitted to the outer end of the tube for permitting retraction of rotation of said fitting to tension or wrap the flexible plastic sleeve or dilation balloon tightly onto the plastic tube for ease of insertion or removal of the catheter.

4. The catheter of claim 1 wherein the catheter further comprises a mark which can be viewed by said radially viewing telescope inserted into said plastic tube of the catheter for precise positioning of the balloon with respect to a prostatic sphincter.

5. The catheter of claim 4 wherein said mark is located on the transparent flexible plastic sleeve or plastic tube of the catheter 6. A method for precisely positioning and pressurizing the steps of:
   providing the prostate balloon dilation catheter of claim 1 which further comprises a mark for positioning said catheter and balloon within a prostatic urethra; and
   inserting said viewing telescope into the transparent tube of said catheter through the outer end of said tube; and
   inserting the catheter with said telescope within a prostatic urethra; and
   introducing sterile fluid into the second fitting; and
   positioning the catheter at a precise location within the prostatic urethra by radially viewing said mark on the catheter through said viewing telescope so as to observe the location of the catheter tube and balloon; and
   introducing fluid pressure to the interior of the first fitting surrounding and slidably fitted to the outer end of the tube thereby pressurizing and dilating the balloon.

7. A prostate balloon dilation catheter comprising:
   a transparent plastic tube having an open inner end and an open outer end; and
   a non-compliant transparent flexible plastic sleeve of predetermined shape fitted over the tube, a portion of said sleeve forming a dilation balloon having a diameter greater than said tube, the inner end of the sleeve closest to the inner end of the tube being provided with a liquid tight seal with the tube; and
   a viewing telescope which can be inserted into said tube which provides radial viewing through the tube and the sleeve for precise positioning of the catheter within a prostatic urethra; and
   a first fitting surrounding and slidably fitted to the outer end of the tube, the outer end of the fitting closest to the outer end of the tube being provided with a liquid tight seal with the tube; and
   a liquid tight seal between the outer end of said transparent flexible plastic sleeve and the fitting; and
   means permitting introduction of dilation fluid to the interior of the first fitting; and
   a liquid passage between the interior of the fitting and the interior of the sleeve to permit pressurization by the fluid of the dilation balloon; and
   a second fitting bonded to the outer end of the transparent plastic tube being provided with a second liquid tight seal with respect to the exterior surface of said viewing telescope inserted into said plastic tube; and
   means permitting introduction of sterile fluid to the interior of the second fitting: and
   a liquid passage between the interior of the second fitting and the exterior surface of the viewing telescope to permit the flow of fluid within the area between the transparent plastic tube and said telescope.

8. The catheter of claim 7 which contains a mark which can be viewed by the radially viewing telescope for precise positioning of the balloon with respect to a prostatic sphincter.

9. The catheter of claim 8 wherein said mark is located on the transparent plastic sleeve or plastic tube.

10. A method for precisely positioning and pressurizing a dilation balloon within the prostatic urethra comprising the steps of:
   providing the prostate balloon dilation catheter of claim 7 which further contains a mark for positioning said catheter and balloon within a prostatic urethra; and
   inserting the viewing telescope into the transparent tube of said catheter through the outer end of said tube; and
   introducing sterile fluid into the second fitting; and
   positioning the catheter at a precise location within the prostatic urethra by radially viewing said mark on the catheter through said viewing telescope so as to observe the location of the catheter tube and balloon; and
   introducing fluid pressure to the interior of the first fitting surrounding and slidably fitted to the outer end of the tube thereby pressurizing and dilating the balloon.

* * * * *